United States Patent [19]

Chan et al.

[11] Patent Number: 5,568,253
[45] Date of Patent: Oct. 22, 1996

[54] SAMPLE HOLDER FOR SAMPLE TESTING APPARATUS

[75] Inventors: Shu F. Chan; Min H. Tsao; Kuo Y. Hsu; Huei C. Peng, all of Hsin-chu, Taiwan

[73] Assignee: Taiwan Semiconductor Manufacturing Company Ltd., Hsin-chu, Taiwan

[21] Appl. No.: 618,892

[22] Filed: Mar. 20, 1996

[51] Int. Cl.⁶ ..................................... G01N 1/10
[52] U.S. Cl. ..................... 356/246; 250/328; 250/341.1
[58] Field of Search .................................. 356/244, 246; 422/64; 250/328, 341, 339; 353/117

[56] References Cited

U.S. PATENT DOCUMENTS

| | | | |
|---|---|---|---|
| 4,042,303 | 8/1977 | Huber | 356/85 |
| 4,042,338 | 8/1977 | Huber | 23/259 |
| 4,580,896 | 4/1986 | Brickus | 356/246 |
| 5,077,013 | 12/1991 | Guigan | 422/64 |
| 5,314,825 | 5/1994 | Weyrauch | 436/43 |
| 5,369,717 | 11/1994 | Attridge | 385/12 |
| 5,457,527 | 10/1995 | Manns et al. | 356/246 |

Primary Examiner—Frank Gonzalez
Assistant Examiner—Michael Stafira
Attorney, Agent, or Firm—George O. Saile; William S. Robertson

[57] ABSTRACT

A holder for samples to be analyzed in a spectrometer is made of a polymer to avoid introducing metal contaminates into the test from the usual metal holder. The preferred polymer is polyvinylidenefluoride (PDVF). The holder uses less expensive polymers for components that do not require the properties of PDVF, and it is constructed to permit replacing parts made of PDVF that have become damaged.

13 Claims, 2 Drawing Sheets

SAMPLE HOLDER FOR SAMPLE TESTING APPARATUS

FIELD OF THE INVENTION

This invention relates to apparatus for handling a sample undergoing a chemical or physical test and more specifically it relates to a sample holder.

1. Introduction

A flameless atomic absorption spectrometer is an example of an apparatus that performs a test on a liquid that is held in a vial. It is used for example for detecting aluminum and other metals. The vials are held in a sample holder while they are processed in the spectrometer.

In a typical use of a sample holder, a work station for filling the samples with the liquid is located several meters away from the spectrometer or other apparatus that performs the test. At the work station, the vials are filled with the samples and the sample holder with the vials is then carried to the apparatus and the test is performed.

Two other examples of apparatus that use a sample holder are a graphite furnace atomic absorption spectrometer (FGAAS) and an electro-thermal-vaporization induced couple plasma mass spectrometer (ETV-ICP-MS).

2. The Prior Art

U.S. Pat. No. 4,042,303 teaches apparatus for carrying a sample holder for use with a graphite furnace atomic absorption spectrometer. A circular turn table 16 is carried by a rotatable shaft 18. The turn table has appreciable thickness and coaxial cylindrical holes are formed near its edge. A part 22 rides against a spring in each hole and carries an arm 26 that extends radially outward from the turn table and has a ring for carrying a cone-shaped sample holder 32.

U.S. Pat. No. 4,042,338 teaches apparatus for filling containers with a liquid that is to be tested with a flameless atomic absorption spectrometer. A disk shaped holder 10 for several containers has several circular openings near its edge, and a sample container 12 is carried in each opening. The disk is rotatable for carrying the samples past a station for filling the containers.

In a third example of a sample holder of the prior art, a disk has circular holes for holding vials that hold the liquid samples. A vial is supported in the disk by a lip that overhangs the edge of the hole. The disk is removably attached to a drive that rotates the disk through the testing apparatus. Commonly, the sample holders of the prior art are made of aluminum.

SUMMARY OF THE INVENTION

We have discovered that aluminum from the holder can be a source of contamination in these tests. Some of the liquids vaporize easily at room temperature. They tend to condense on parts of the sample holder (the base and the central support, described later) and they vaporize from these locations and condense again at any point. The process of vaporization and condensation erodes aluminum from an aluminum sample holder, and it is the main source of this contamination of the samples.

Aluminum is one of the metals that the test detects and the tests detect very small amounts of a metal. One object of this invention is to provide a new sample holder that can be constructed of a material other than aluminum.

Another object of this invention is to provide a sample holder that can be formed with a polymer. Using a polymer avoids other metals that are commonly detected with this apparatus: iron, copper, nickel, sodium, potassium and calcium.

The preferred polymer is polyvinylidenefluoride (PDVF). PVDF is an expensive polymer, and the sample holder of this invention is organized so that components of the sample holder that do not directly contact the vapor are preferably made of less expensive materials. More specifically, a base and a cover are made of less expensive materials (preferably, nylon and polycarbonate respectively).

Other objects and features of the invention will appear in the description of the preferred embodiment.

THE DRAWING

THE PREFERRED EMBODIMENT

Figure 1:
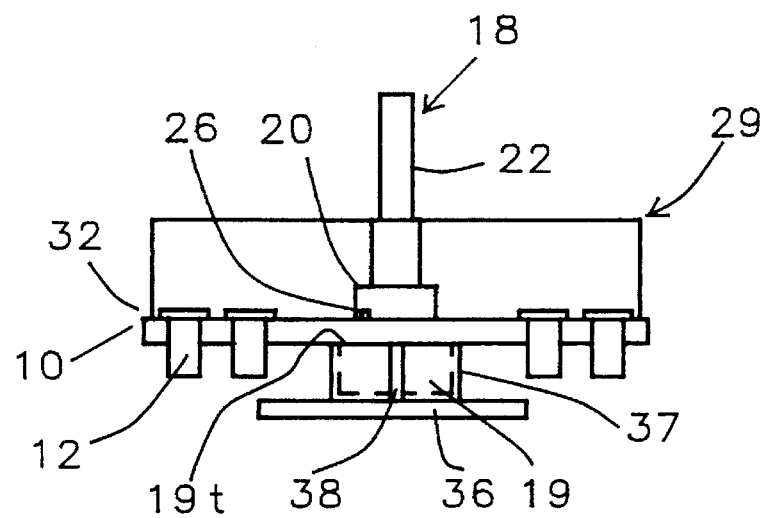
FIG. 1 is a side view of the preferred sample holder of this invention.

The sample holder includes a thin disk 10 that has circular openings 11 that each can carry one vial 12. The vial used in these tests commonly is made of polyethylene (PE), polystyrene (PS) or PVDF. (Glass is not used because it is affected by some acids and contaminates the samples.) The vial has cylindrical side walls, a circular bottom and an open top with a lip that extends radially beyond the outer surface of a wall to overhang the part of the disk at the edge of the hole that underlies the lip.

The circular openings 11 are located in the outer part of the disk at a radius to carry a vial into a processing station. In the disk of the drawing, the openings 11 are arranged in two circles, an outer circle 15 and an inner circle 16. The openings are concentric with the axis of the disk and are equally spaced along the circles so that the disk can be rotated with a stepping drive that brings the vials into a testing position. The preferred disk holds twenty vials in the outer circle 15 and twenty vials (more closely spaced) in the inner circle 16.

The disk is preferably made of PVDF and it is formed separately from other components that will be described next.

The disk is carried by a central support 18. The support has four cylindrical sections 19, 20, 21, and 22 that are progressively narrower in diameter from bottom to top. They will be called the lower (19), lower intermediate (20) upper intermediate (21) and upper (22) sections. Where a smaller diameter section is joined to a larger diameter section, the lower section forms an upward facing annular ledge identified with a reference character having the numeral of the section and the letter suffix t (for top).

The top section 22 forms a convenient handle for carrying the sample holder. The disk has a center hole 25 that adapts the disk to be held radially by the cylindrical wall of section 20 and to be supported by ledge 19t of the lower section. The lower cylindrical section 19 and the inner edge of hole 25 are adapted to receive a tenon 26 that tenons the disk to the center support.

The horizontal surface of ledge 20t of the lower intermediate section 20 is not used, but separate sections 20 and 21 (as contrasted with a single intermediate section with the diameter of lower intermediate section 20) provides additional clearance when the sample holder is mounted in a sample tester. However, from a more general standpoint, the sample holder has an intermediate section that is formed with upper and lower parts.

Figure 2:
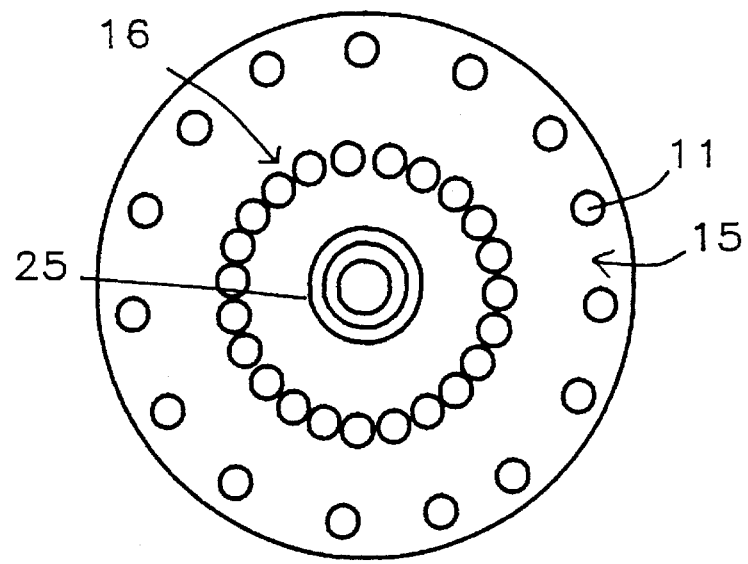
FIG. 2 is a top view of the sample holder of FIG. 1.
Figure 3:
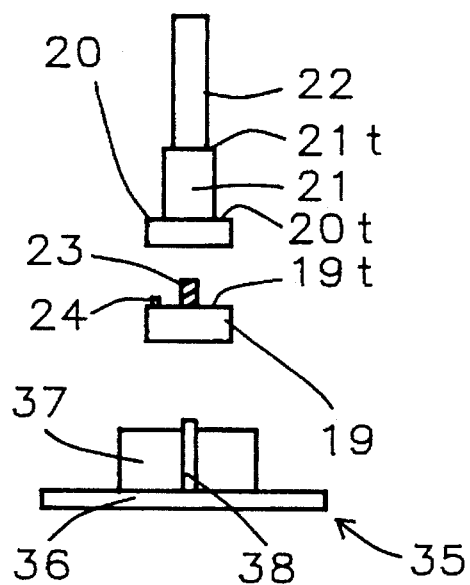
FIG. 3 is an exploded view of some of the components of the sample holder of FIG. 1.

The central support is made in two separable parts so that one of the parts can be replaced it becomes damaged. Preferably, as FIG. 2 shows, sections 20, 21 and 22 are formed as a unit that is separable from section 19. The lower section 19 is connected to the lower intermediate section 20 by means of a bolt 23 that extends upward from section 19. Section 20 has threads (not shown) that receive the bolt. A tenon 24 prevents relative rotation between sections 19 and 20.

Figure 4:
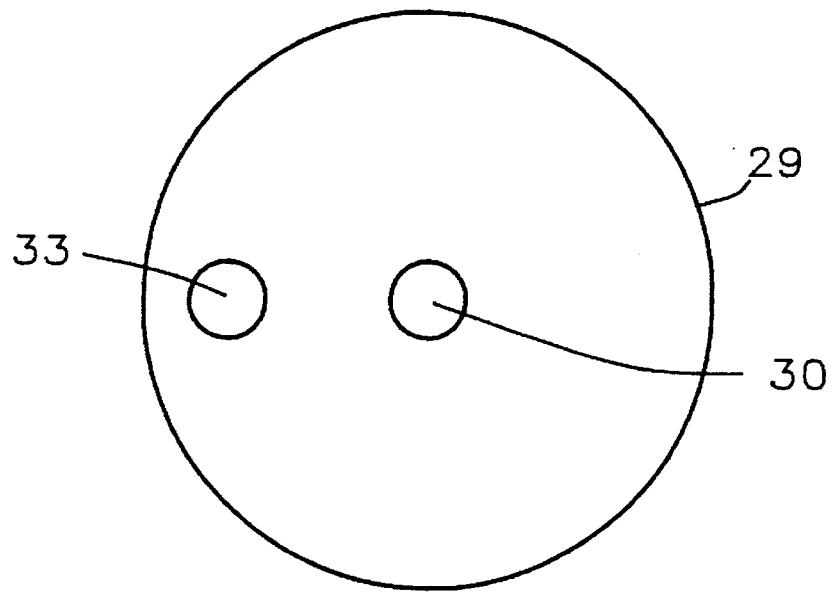
FIG. 4 is a top view of a component of FIG. 1.

A cover 29 is in the form of an inverted cup with a center hole 30 that fits over upper support section 22 and rests on the ledge 21t of the upper intermediate section 21. The downwardly facing rim 32 of the cover forms a seal with the upper surface of disk 10 at a radius outside the vials. The cover has a suitable opening 33 for accessing the underlying vials and FIG. 4 shows a representative opening 33.

The preferred material for the cover is polycarbonate because it is transparent (as the drawing represents) and permits easy inspection of the vials.

The sample holder includes a base 35 that is formed separately from the center shaft 18 and the disk 10. The lower section 19 and the base 35 are adapted to fit together releasably. The base is in the form of a lower disk part 36 and an upward facing cup part 37. The center support lower part 19 fits into the cup part 37, and these parts are held together with tenons 38. The base can be attached to a bench located at the work station where the vials are filled, and the sample holder is carried to the test station without the base. The base holds the central support to prevent tipping the holder if the vials are loaded in a sequence that would otherwise unbalance the holder. Since the base does not enter the test station, it does not need to be made of PVDF an it is preferably formed of nylon (because it is less expensive than PVDF and is otherwise suitable).

Other Embodiments

From the description of a preferred embodiment of the invention, those skilled in the art will recognize modifications within the spirit of the invention and the intended scope of the claims.

What is claimed is:

1. A holder for vials containing a liquid to be tested while the vials are held in the holder, comprising, a support having a bottom cylindrical section of a predetermined diameter, a middle cylindrical section of a smaller diameter than the bottom section, and a top cylindrical section of a smaller diameter than the middle section, whereby a lower annular ledge is formed between the bottom section and the middle section and an upper annular ledge is formed between the middle section and the top section, a disk having a center hole adapting the disk to fit over the middle section and to be supported by the lower ledge, the disk having means for holding vials, the disk being made of a polymer and being substantially free of materials that are to be detected during the test, and a cover made of a polymer and having an inverted cup shape and having a center hole for locating the cover on the top section of the support with the edge of the cover sealing with the upper surface of the disk at a radius beyond the vial supporting means.

2. The holder of claim 1 wherein the means for holding vials comprises holes formed in the disk to receive the vials and wherein the vials have a lip overhanging the edge of the hole.

3. The holder of claim 1 including a base for receiving the bottom section of the support to prevent the holder from tipping while it is being loaded with samples.

4. The holder of claim 3 wherein the base has a cup shaped part adapted to receive the bottom section of the support and a flat disk shaped support for holding the cup shaped part in a suitable position.

5. The holder of claim 4 including a tenon for holding the support bottom section to the cup shaped part of the base.

6. The holder of claim 4 wherein the polymer of the disk is PVDF.

7. The holder of claim 6 wherein the polymer of the support is PVDF.

8. The holder of claim 4 wherein the middle section is formed as an upper part and a lower part.

9. The holder of claim 8 wherein the top section forms a handle for carrying the sample holder by hand.

10. The holder of claim 9 wherein the disk and support are joined with tenons.

11. The holder of claim 9 wherein the top support section and the middle support section are formed as a unit and the bottom support is separable from the top and middle support sections for replacing a damaged part of the support.

12. The holder of claim 9 including a bolt extending upward from the support bottom section and threads for receiving bolt in the middle section lower part.

13. The holder of claim 12 wherein the cover is formed of a transparent polymer.

* * * * *

UNITED STATES PATENT AND TRADEMARK OFFICE
CERTIFICATE OF CORRECTION

PATENT NO. : 5,568,253
DATED : 10/22/96
INVENTOR(S) : Shu F. Chan, Min H. Tsai, Kuo Y. Hsu and Huei C. Peng It is certified that error appears in the above-indentified patent and that said Letters Patent is hereby corrected as shown below: Title page:

Item (75), correct inventor's name from "Min H. Tsao" to --Min H. Tsai--

Signed and Sealed this

Twenty-sixth Day of August, 1997

*Attest:*

*Attesting Officer*

BRUCE LEHMAN

*Commissioner of Patents and Trademarks*